United States Patent [19]

Regel et al.

[11] Patent Number: 4,587,239
[45] Date of Patent: May 6, 1986

[54] 1-AZOLYL-3-PYRAZOLYL-2-PROPANOL FUNGICIDES

[75] Inventors: Erik Regel, Wuppertal; Karl H. Büchel, Burscheid; Paul Reinecke, Leverkusen; Wilhelm Brandes, Leichlingen, all of Fed. Rep. of Germany

[73] Assignee: Bayer Aktiengesellschaft, Leverkusen, Fed. Rep. of Germany

[21] Appl. No.: 592,162

[22] Filed: Mar. 22, 1984

[30] Foreign Application Priority Data

Apr. 12, 1983 [DE] Fed. Rep. of Germany ....... 3313073

[51] Int. Cl.⁴ .................. C07D 403/06; C07D 231/12; A01N 43/56; A01N 43/653
[52] U.S. Cl. .................................... 514/184; 514/189; 514/190; 514/191; 514/383; 514/397; 514/406; 548/101; 548/102; 548/262; 548/336; 548/374
[58] Field of Search ............... 548/374, 336, 262, 101, 548/102; 424/273 P, 273 R, 269; 514/383, 397, 406, 184, 189, 190, 191

[56] References Cited

U.S. PATENT DOCUMENTS

| | | | |
|---|---|---|---|
| 2,979,512 | 4/1961 | Wright | 548/374 |
| 4,049,418 | 9/1977 | Timmler et al. | 548/262 |
| 4,118,487 | 10/1978 | Regel et al. | 424/269 |
| 4,138,243 | 2/1979 | Bohner et al. | 424/269 |
| 4,229,460 | 10/1980 | Heeres et al. | 424/269 |
| 4,359,469 | 11/1982 | Stetter et al. | 424/269 |
| 4,507,140 | 3/1985 | Sugavanam | 548/336 |

FOREIGN PATENT DOCUMENTS 0044605 1/1982 European Pat. Off. ............ 424/269

Primary Examiner—Richard A. Schwartz
Assistant Examiner—Kurt G. Briscoe
Attorney, Agent, or Firm—Sprung Horn Kramer & Woods

[57] ABSTRACT

1-Azolyl-3-pyrazolyl-2-propanol derivatives of the general formula

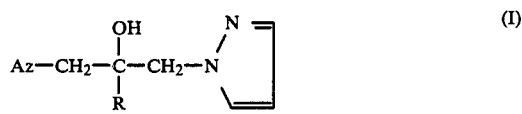

in which
Az represents 1,2,4-triazol-1-yl, imidazol-1-yl or pyrazol-1-yl and
R represents alkyl, alkenyl, alkinyl, optionally substituted phenyl, optionally substituted phenylalkyl, optionally substituted phenylalkenyl, optionally substituted phenylalkinyl, naphthyl or optionally substituted cycloalkyl, and acid addition salts and metal salt complexes thereof, which possess fungicidal activity. Oxirane intermediates lacking Az are also new.

11 Claims, No Drawings

1-AZOLYL-3-PYRAZOLYL-2-PROPANOL FUNGICIDES

The present invention relates to new 1-azolyl-3-pyrazolyl-2-propanol derivatives, several processes for their preparation and their use as fungicides.

It has already been disclosed that certain 1,3-diazolyl-2-propanol derivatives, such as, for example, 1,3-di(1,2,4-triazol-1-yl)-2-(4-chlorophenyl)-2-propanol, have good fungicidal properties (compare EP-OS (European Published Specification) No. 0,044,605). However, the action of these compounds is not always completely satisfactory, especially when low amounts and concentrations are used.

New 1-azolyl-3-pyrazolyl-2-propanol derivatives of the general formula

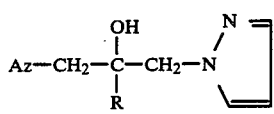  (I)

in which

Az represents 1,2,4-triazol-1-yl, imidazol-1-yl or pyrazol-1-yl and

R represents alkyl, alkenyl, alkinyl, optionally substituted phenyl, optionally substituted phenylalkyl, optionally substituted phenylalkenyl, optionally substituted phenylalkinyl, naphthyl or optionally substituted cycloalkyl, and acid addition salts and metal salt complexes thereof, have been found.

It has furthermore been found that the 1-azolyl-3-pyrazolyl-2-propanol derivatives of the formula (I) are obtained by a process in which (a) 2-azolylmethyl-oxiranes of the formula

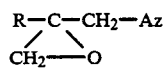  (II)

in which

Az and R have the abovementioned meaning, are reacted with azoles of the formula

  (III)

in which

Az' has the meanings of Az, but Az and/or Az' represent pyrazol-1-yl, in the presence of an alkali metal alcoholate and in the presence of a diluent, or (b) 2-halogenomethyl-oxiranes of the formula

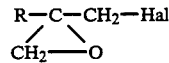  (IV)

in which

R has the abovementioned meaning and

Hal represents halogen, are reacted with pyrazole of the formula

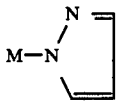  (V)

in which

M represents hydrogen or an alkali metal, in the presence of a diluent and, if appropriate, in the presence of an acid-binding agent, or (c) dihalogenoalkanols of the formula

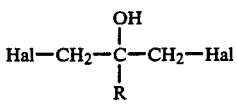  (VI)

in which

Hal and R have the abovementioned meaning, are reacted with pyrazole of the formula (V) in the presence of a diluent and, if appropriate, in the presence of an acid-binding agent.

If appropriate, an acid or a metal salt can then be added on to the compounds of the formula (I) thus obtained.

Surprisingly, the compounds of the formula (I) according to the invention exhibit a better fungicidal activity than 1,3-di-(1,2,4-triazol-1-yl)-2-(4-chlorophenyl)-2-propanol, which is known from the prior art and is a closely related compound structurally and from the point of view of its action. The active compounds according to the invention thus represent an enrichment of the art.

Formula (I) provides a general definition of the 1-azolyl-3-pyrazolyl-2-propanol derivatives according to the invention. Preferably, in this formula, Az represents 1,2,4-triazol-1-yl, imidazol-1-yl or pyrazol-1-yl and R represents straight-chain or branched alkyl with 1 to 12 carbon atoms, straight-chain or branched alkenyl or alkinyl with in each case 2 to 6 carbon atoms, or phenyl, phenylalkyl with 1 to 4 carbon atoms in the alkyl part, phenylalkenyl with 2 to 4 carbon atoms in the alkenyl part or phenylalkinyl with 2 to 4 carbon atoms in the alkinyl part, each of which is optionally mono-, di- or tri-substituted in the phenyl part by identical or different substituents, substituents on the phenyl which may be mentioned in each case being: halogen, alkyl with 1 to 4 carbon atoms, alkoxy and alkylthio with in each case 1 or 2 carbon atoms, alkoxyalkyl with 1 or 2 carbon atoms in each alkyl part and phenyl which is optionally substituted by halogen; or represents naphthyl, or cycloalkyl which has 3 to 7 carbon atoms and is optionally substituted by alkyl with 1 to 4 carbon atoms.

Particularly preferred compounds of the formula (I) are those in which

Az represents 1,2,4-triazol-1-yl, imidazol-1-yl or pyrazol-1-yl and

R represents ethyl, tert.-butyl, allyl or propargyl, or phenyl, benzyl, phenethyl, phenethenyl or phenethinyl, each of which is optionally monosubstituted or disubstituted in the phenyl part by identical or different substituents, substituents on the phenyl which may be mentioned in each case being: fluorine, chlorine, methyl, methoxy, methylthio, isopropoxy, methoxymethyl, phenyl which is optionally substituted by fluorine or chlorine, naphthyl, and cyclopropyl, cyclopentyl and cyclohexyl, each of which is optionally substituted by methyl or ethyl.

Very particularly preferred compounds of the formula (I) are those in which

Az represents 1,2,4-triazol-1-yl, imidazol-1-yl or pyrazol-1-yl and

R represents phenyl which is optionally monosubstituted or disubstituted by identical or different substituents, substituents which may be mentioned being: fluorine, chlorine, methyl and methoxy.

Addition products of acids and those 1-azolyl-3-pyrazol-2-propanol derivatives of the formula (I) in which the substituents Az and R have the meanings which have already been mentioned as preferred for these substituents are also preferred compounds according to the invention.

Preferred acids which can be added on include hydrogen halide acids, such as, for example, hydrochloric acid and hydrobromic acid, in particular hydrochloric acid, and furthermore phosphoric acid, nitric acid, monofunctional and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acids, such as p-toluenesulphonic acid and 1,5-naphthalenedisulphonic acid.

Other preferred compounds according to the invention are addition products of salts and metals of main groups II to IV and sub-groups I and II and IV to VIII and those 1-azolyl-3-pyrazolyl-2-propanol derivatives of the formula (I) in which the substituents Az and R have the meanings which have already been mentioned as preferred for these substituents.

Particularly preferred salts here are those of copper, zinc, manganese, magnesium, tin, iron and nickel. Possible anions of these salts are those which are derived from acids leading to physiologically acceptable addition products. In this connection, particularly preferred acids of this type are the hydrogen halide acids, such as, for example, hydrochloric acid and hydrobromic acid, and nitric acid and sulphuric acid.

If, for example, 2-(2-chlorophenyl)-2-(1,2,4-triazol-1-yl-methyl)-oxirane, potassium tert.-butylate and pyrazole are used as starting substances, the course of the reaction in process (a) according to the invention can be represented by the following equation:

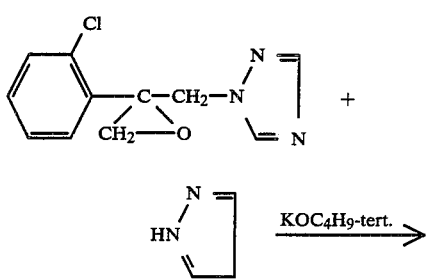

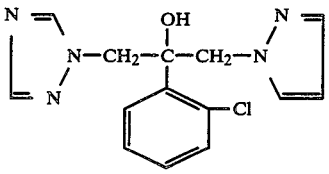

If, for example, 2-chloromethyl-2-(4-chlorophenyl)-oxirane and pyrazole are used as starting substances and potassium carbonate is used as the acid-binding agent, the course of the reaction in process (b) according to the invention can be represented by the following equation:

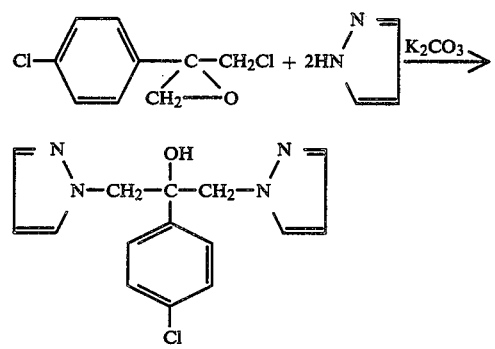

If, for example, 1,3-dichloro-2-(4-chlorophenyl)-2-propanol and pyrazole are used as starting substances and potassium carbonate is used as the acid-binding agent, the course of process (c) according to the invention can be represented by the following equation:

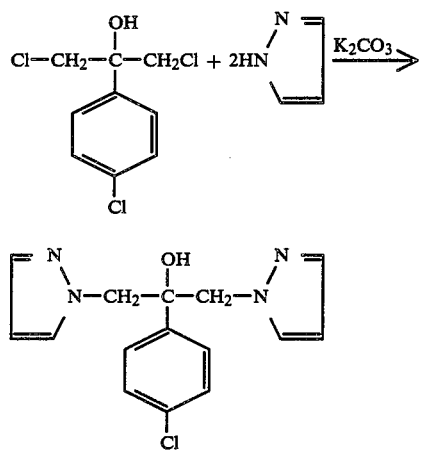

Formula (II) provides a general definition of the 2-azolylmethyl-oxiranes to be used as starting substances for process (a) according to the invention. In this formula, Az and R preferably represent those radicals which have already been mentioned as preferred for these substituents in connection with the description of the substances of the formula (I) according to the invention.

Some of the azolylmethyl-oxiranes of the formula (II) are known (compare, for example, European Pat. No. 0,044,605 and European Pat. No. 0,061,835). The 2-pyrazolylmethyl-oxiranes of the formula

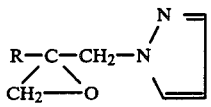
(IIa)

in which

R has the abovementioned meaning, are not yet known.

The 2-azolylmethyl-oxiranes of the formula (II) can be obtained by a process in which 2-halogenomethyloxiranes of the formula (IV) are reacted with azoles of the formula (III) in the presence of an inert organic solvent, such as, for example, acetone, and in the presence of an acid-binding agent, such as, for example, potassium carbonate, at temperatures between 20° and 120° C. (compare also the preparation examples).

The 2-azolylmethyl-oxiranes of the formula (II) can also be obtained in a generally known manner, by a process in which azolo-ketones of the formula $$R-CO-CH_2-Az \quad (VII)$$

in which

Az and R have the abovementioned meaning, either (α) are reacted with dimethyloxosulphonium methylide of the formula

(VIII)

in a manner which is known per se, in the presence of a diluent, such as, for example, dimethylsulphoxide, at temperatures between 20° and 80° C. (in this context, compare the statements in J. Am. Chem. Soc. 87, 1363–1364 (1965)), or (β) are reacted with trimethylsulphonium methylsulphate of the formula $$[(CH_3)_3S^{(+)}]CH_3SO_4^{(-)} \quad (IX)$$

in a manner which is known per se, in the presence of an inert organic solvent, such as, for example, acetonitrile, and in the presence of a base, such as, for example, sodium methylate, at temperatures between 0° and 60° C., preferably at room temperature (compare also the statements in Heterocyclus 8, 397 (1977)).

If appropriate, the oxiranes of the formula (II) thus obtained can be further reacted directly, without being isolated.

Ketones of the formula (VII) required as starting substances in the preparation of the 2-azolylmethyl-oxiranes of the formula (II) are known (compare, for example DE-OS (German Published Specification No. 2,431,407, DE-OS (German Published Specification) No. 2,638,470 and they are the subject of U.S. application Ser. No. 328,871, filed Dec. 8, 1981, now pending, and can be prepared by processes which are known in principle.

The dimethyloxosulphonium methylide of the formula (VIII) required in process variant (α) is likewise known (compare J. Am. Chem. Soc. 87, 1363–1364 (1965)). In the above reaction, it is processed in the freshly prepared state by being produced in situ by reacting trimethyloxosulphonium iodide with sodium hydride or sodium amide, in particular with potassium tert.-butylate or sodium methylate, in the presence of a diluent.

The trimethylsulphonium methylsulphate of the formula (IX) required in process variant (β) is likewise known compare Heterocycles 8, 397 (1977)). In the above reaction, it is likewise employed in the freshly prepared state, by being produced in situ by reaction of dimethyl sulphide with dimethyl sulphate.

The azoles of the formula (III) are generally known compounds of organic chemistry.

Formula (IV) provides a general definition of the 2-halogenomethyl-oxiranes to be used as starting substances for process (b) according to the invention. In this formula, R preferably represents those radicals which have already been mentioned as preferred for these substituents in connection with the description of the substances of the formula (I) according to the invention. Hal preferably represents chlorine, bromine or iodine.

2-Halogenomethyl-oxiranes of the formula (IV) are known, and they can be obtained in a generally known manner, by adding aqueous alkali metal hydroxide solution to dihalogenoalkanols of the formula (VI) (in this context, compare also J. Org. Chem. 27, 2242 (1961)).

Formula (V) provides a general definition of the azoles also to be used as starting substances for process (b) according to the invention. In this formula, M preferably represents hydrogen, sodium or potassium.

The azoles of the formula (V) are generally known compounds of organic chemistry. The alkali metal salts are obtained by reacting pyrazole, imidazole or 1,2,4-triazole with sodium ethylate or potassium ethylate, or by reacting pyrazole, imidazole or 1,2,4-triazole with the equivalent amount of the corresponding alkali metal hydride.

Formula (VI) provides a general definition of the dihalogenoalkanols to be used as starting substances for process (c) according to the invention. In this formula, R preferably represents those radicals which have already been mentioned as preferred for this substituent in connection with the description of the substances of the formula (I) according to the invention. Hal preferably represents chlorine.

Dihalogenoalkanols of the formula (VI) are known, and they can be obtained in a generally known manner, by reacting 1,3-dihalogenoacetones, such as, in particular, 1,3-dichloroacetone, with a corresponding Grignard reagent (in this context, compare also J. Org. Chem. 27, 2242 (1961)).

Preferred possible diluents for process (a) according to the invention are inert organic solvents. These include, preferably, nitriles, such as, in particular, acetonitrile; aromatic hydrocarbons, such as benzene, toluene and dichlorobenzene; formamides, such as, in particular, dimethylformamide; halogenated hydrocarbons, such as methylene chloride or carbon tetrachloride; and hexamethylphosphoric acid triamide.

Process (a) according to the invention is carried out in the presence of an alkali metal alcoholate. Preferred alkali metal alcoholates include the methylates and ethylates of sodium and potassium and, in particular, also potassium tert.-butylate.

The reaction temperatures can be varied within a substantial range in carrying out process (a) according to the invention. In general, the reaction is carried out between about 30° and 150° C., preferably between 80° and 100° C.

In carrying out process (a) according to the invention, 1 to 4 mols of azole of the formula (III) and 1 to 4 mols of alkali metal alcoholate are preferably employed per mol of oxirane of the formula (II). The end products are isolated in a generally customary manner.

In a preferred embodiment of process (a) according to the invention, the oxiranes of the formula (II) obtained according to process ($\alpha$) or ($\beta$) are further reacted directly, without being isolated.

Preferred possible diluents for processes (b) and (c) according to the invention are inert organic solvents. These include, preferably, ketones, such as, in particular, acetone and methyl ethyl ketone; nitriles, such as, in particular, acetonitrile; alcohols, such as, in particular, ethanol and isopropanol; ethers, such as, in particular, tetrahydrofuran or dioxane; formamides, such as, in particular, dimethylformamide; and aromatic and halogenated hydrocarbons.

If appropriate, processes (b) and (c) according to the invention are carried out in the presence of an acid-binding agent. All the inorganic or organic acid-binding agents which can usually be employed can be added, such as alkali metal carbonates, for example sodium carbonate and potassium carbonate; or such as lower tertiary alkylamines, cycloalkylamines, cycloalkylamines or arylalkylamines, for example triethylamine, N,N-dimethylcyclohexylamine, dicyclohexylamine or N,N-dimethylbenzylamine, and furthermore pyridine and diazabicyclooctane, and also an appropriate excess of azole.

The reaction temperatures can be varied within a substantial range in carrying out processes (b) and (c) according to the invention. In general, the reactions are carried out between about 20° and about 150° C., preferably at 20° to 120° C.

In carrying out processes (b) and (c) according to the invention, 2 to 4 mols of azole of the formula (V) and, if appropriate, 2 to 4 mols of acid-binding agent are employed per mol of the 2-halogenomethyloxiranes of the formula (IV) or of the dihalogenoalkanols of the formula (VI). The compounds of the formula (I) are isolated in a customary manner.

The acid addition salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtration, and if appropriate purified by washing with an inert organic solvent.

The metal salt complexes of the compounds of the formula (I) can be obtained in a simple manner by customary processes, thus, for example, by dissolving the metal salt in alcohol, for example ethanol, and adding the solution to compounds of the formula (I). The metal salt complexes can be isolated in a known manner, for example by filtration, and if necessary purified by recrystallization.

The active compounds according to the invention exhibit a powerful microbicidal action and can be employed in practice for combating undesired microorganisms. The active compounds are suitable for use as plant protective agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protective agents, the active compounds according to the invention can be used with particularly good success for combating cereal diseases such as *Cochliobolus sativus, Erysiphe graminis, Puccinia* and *Pyrenophora teres;* and furthermore for combating apple scab (*Venturia inaequalis*) and rice diseases, such as Pyricularia and Pellicularia.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic materials such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydroly-products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

EXAMPLE 1

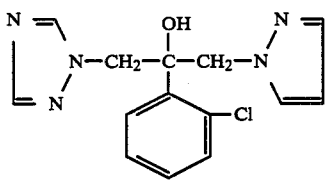

(Process a)

A mixture of 3.4 g (50 mmols) of pyrazole, 2.8 g (25 mmols) of potassium tert.-butylate and 5.9 g (25 mmols) of 2-(2-chlorophenyl)-2-(1,2,4-triazol1-yl-methyl)-oxirane in 200 ml of dimethylformamide is heated at 100° C. for 36 hours. The reaction mixture is then concentrated in vacuo, the residue is dissolved in chloroform and the solution is filtered and washed with water. The chloroform solution is dried over sodium sulphate, filtered and concentrated in vacuo. The residue which remains is purified by chromatography (silica gel 60 Merck/chloroform). 5.8 g (74% of theory) of 2-(2-chlorophenyl)-1-(pyrazol-1-yl)-3-(1,2,4-triazol-1-yl)-2-propanol of refractive index $n_D^{20}$ 1.5690 are obtained.

Preparation of the starting substance

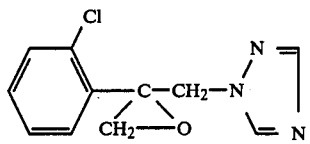

A solution of 68.5 g (0.33 mol) of 2-(2-chlorophenyl)-2-chloromethyl-oxirane in 50 ml of acetone is added dropwise to a mixture of 24.2 g (0.35 mol) of triazole and 48.3 g (0.35 mol) of potassium carbonate in 300 ml of acetone. The reaction mixture is heated under reflux for 20 hours and filtered and the filtrate is concentrated. The residue is dissolved in methylene chloride and the solution is washed with water, dried over sodium sulphate, filtered and concentrated again. The residue is purified by column chromatography (silica gel 60 Merck/chloroform). 159 g (20.5% of theory) of 2-(2-chlorophenyl)-2-(1,2,4-triazol-1-yl-methyl)-oxirane of refractive index $n_D^{20}$ 1.5572 are obtained.

The following compounds of the general formula

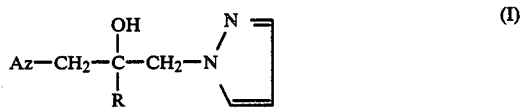

are obtained in a corresponding manner:

| Example No. | R | Az | Melting point (°C.) |
|---|---|---|---|
| 2 | Cl—⟨phenyl⟩— | pyrazol-1-yl | 118 |
| 3 | 2-Cl-phenyl | pyrazol-1-yl | 100 |

USE EXAMPLES

The compound shown below is employed as the comparison substance in the use examples which follow:

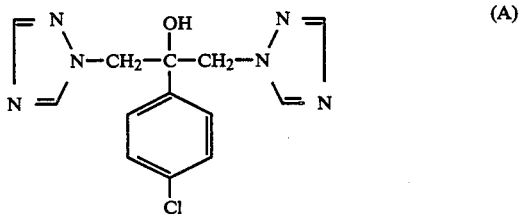

EXAMPLE A

*Cochliobolus sativus* test (barley)/protective
Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of *Cochliobolus sativus*. The plants remain in an incubation cabinet for 48 hours at 20° C. and 100% relative atmospheric humidity.

The plants are placed in a greenhouse at a temperature of about 20° C. and a relative atmospheric humidity of about 80%.

Evaluation is carried out 7 days after the inoculation.

In this test, a clearly superior activity compared with the prior art is shown, for example, by the compound according to the following preparation example: 1.

EXAMPLE B

Venturia test (apple)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the applie scab causative organism (*Venturia inaequalis*) and then remain in an incubation cabinet at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, a clearly superior activity compared with the prior art is shown, for example, by the compound according to the following preparation example: 1.

It is understood that the specification and examples are illustrative but not limitative of the present invention and that other embodiments within the spirit and scope of the invention will suggest themselves to those skilled in the art.

We claim:

1. A 1-azolyl-3-pyrazolyl-2-propanol derivative of the formula

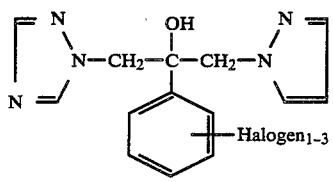

or an addition product thereof with an acid or metal salt.

2. A compound or addition product according to claim 1,
in which halogen is one or two fluorine or chlorine atoms.

3. A compound according to claim 1, wherein such compound is 2-(2-chlorophenyl)-1-(pyrazol-1-yl)-3-(1,2,4-triazol-1-yl)-2-propanol of the formula

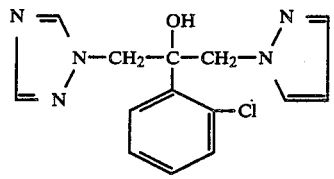

or an addition product thereof with an acid or metal salt.

4. A 1-azolyl-3-pyrazolyl-2-propanol derivative of the formula

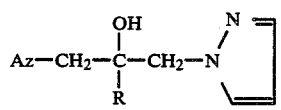

in which
Az represents 1,2,4-triazol-1-yl, imidazol-1-yl or pyrazol-1-yl and
R represents alkenyl or alkinyl with in each case 2 to 6 carbon atoms, phenylalkenyl with 2 to 4 carbon atoms in the alkenyl part or phenylalkinyl with 2 to 4 carbon atoms in the alkinyl part, each of which is optionally mono-, di- or tri-substituted in the phenyl part by identical or different substituents from the group consisting of halogen, alkyl with 1 to 4 carbon atoms, alkoxy and alkylthio with in each case 1 to 2 carbon atoms, alkoxyalkyl with 1 or 2 carbon atoms in each alkyl part and optionally halogen-substituted phenyl, or an addition product thereof with an acid or metal salt.

5. A fungicidal composition comprising a fungicidally effective amount of a compound or addition product according to claim 1 in admixture with a diluent.

6. A fungicidal composition comprising a fungicidally effective amount of a compound or addition product according to claim 4 in admixture with a diluent.

7. A method of combating fungi which comprises administering to such fungi or to a fungus habitat a fungicidally effective amount of a compound or addition product according to claim 1.

8. The method according to claim 7, wherein such compound is
2-(2-chlorophenyl)-1-(pyrazol-1-yl)-3-(1,2,4-triazol-1-yl)-2-propanol, or an addition product thereof with an acid or metal salt.

9. A method of combating fungi which comprises administering to such fungi or to a fungus habitat a fungicidally effective amount of a compound or addition product according to claim 4.

10. A 2-pyrazolylmethyl-oxirane of the formula

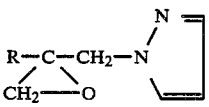

in which

R represents alkenyl or alkinyl with in each case 2 to 6 carbon atoms, phenylalkenyl with 2 to 4 carbon atoms in the alkenyl part or phenylalkinyl with 2 to 4 carbon atoms in the alkinyl part, each of which is optionally mono-, di- or tri-substituted in the phenyl part by identical or different substituents, from the group consisting of halogen, alkyl with 1 to 4 carbon atoms, alkoxy and akylthio with in each case 1 to 2 carbon atoms, alkoxyalkyl with 1 or 2 carbon atoms in each alkyl part and optionally halogen-substituted phenyl, or an addition product thereof with an acid or metal salt.

11. A 2-pyrazolylmethyl-oxirane of the formula

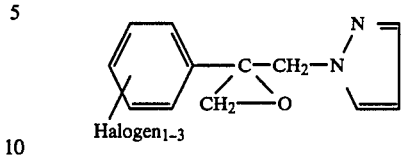

or an addition product thereof with an acid or metal salt.

* * * * *